United States Patent

Hanhijärvi et al.

[11] Patent Number: 5,442,101
[45] Date of Patent: Aug. 15, 1995

[54] METHYLENEBISPHOSPHONIC ACID DERIVATIVES

[75] Inventors: Hannu Hanhijärvi, Turku; Heikki Nupponen, Kangasala; Jouko Vepsäläinen; Esko Pohjala, both of Tampere, all of Finland

[73] Assignee: Leiras Oy, Turku, Finland

[21] Appl. No.: 78,155

[22] PCT Filed: Dec. 18, 1991

[86] PCT No.: PCT/FI91/00396

§ 371 Date: Oct. 20, 1993

§ 102(e) Date: Oct. 20, 1993

[87] PCT Pub. No.: WO92/11268

PCT Pub. Date: Jul. 9, 1992

[30] Foreign Application Priority Data

Dec. 20, 1990 [FI] Finland ................................ 906296

[51] Int. Cl.⁶ .......................... C07F 9/44; A61K 31/66
[52] U.S. Cl. .......................... 562/10; 544/157; 546/21; 558/155; 558/157
[58] Field of Search .............. 562/10; 514/108, 89, 514/90; 558/131, 155, 157; 544/157; 546/21

[56] References Cited

U.S. PATENT DOCUMENTS

| | | | |
|---|---|---|---|
| 3,524,846 | 8/1970 | Moffatt et al. | 260/211.5 |
| 3,808,265 | 4/1974 | Randall et al. | 260/502.4 R |
| 4,293,505 | 10/1981 | Randall | 260/983 |
| 4,814,326 | 3/1989 | Rosini et al. | 514/108 |
| 5,212,164 | 5/1993 | Biller et al. | 514/108 |
| 5,273,969 | 12/1993 | Biller et al. | 514/108 |
| 5,393,748 | 2/1995 | Pohjala et al. | 514/89 |

FOREIGN PATENT DOCUMENTS

A20356866 3/1990 European Pat. Off. .

OTHER PUBLICATIONS

CA92(7):51765k (1979).
Chem. Abstracts, vol. 92, No. 7, 18 (Feb. 1980) p. 27, abstract 51765k.

*Primary Examiner*—José G. Dees
*Assistant Examiner*—B. Frazier
*Attorney, Agent, or Firm*—Wolf, Greenfield & Sacks

[57] ABSTRACT

The invention relates to novel methylenebisphosphonic acid ester amide derivatives of general formula (I), in which formula $W^1$, $W^2$, $W^3$ and $W^4$ are independently the group $OR^1$ or the group $NR^2R^3$ wherein $R^1$, $R^2$ and $R^3$ independently are hydrogen or straight or branched, optionally unsaturated $C_1$-$C_{22}$-alkyl, optionally substituted, optionally unsaturated $C_3$-$C_{10}$-cycloalkyl, aryl, aralkyl or silyl $SiR_3$, or the groups $R^2$ and $R^3$ form together with the adjacent nitrogen atom a 3 to 10-membered saturated, partly saturated or aromatic heterocyclic ring, wherein in addition to the nitrogen atom, there may be one or two heteroatoms from the group N, O and S, provided that in formula (I) at least one of the groups $W^1$, $W^2$, $W^3$ and $W^4$ is hydroxy and at least one of the groups $W^1$, $W^2$, $W^3$ and $W^4$ is amino group $NR^2R^3$, $Q^1$ and $Q^2$ are independently hydrogen, fluorine, chlorine, bromine or iodine, including the stereoisomers, such as the geometrical isomers and the optically active isomers, of the compounds, as well as the pharmacologically acceptable salts of the compounds.

6 Claims, No Drawings

METHYLENEBISPHOSPHONIC ACID DERIVATIVES

This is a 35 U.S. C. of PCT/FI91/00396, filed Dec. 18, 1991, now WP92/11268.

This invention concerns novel methylenebisphosphonic acid derivatives, in particular novel halogen substituted methylenebisphosphonic acid amides and ester amides, processes for the preparation of these novel compounds, as well as pharmaceutical compositions comprising these novel compounds.

Several publications disclose methylenebisphosphonic acids, their salts and some tetraesters, but there are only a few disclosures of corresponding partial esters, partial amides and partial ester amides.

The preparation of tetraesters of methylenebisphosphonic acids has been described in the publications: J. Am. Chem. Soc. 78, (1956) 4450; J. Chem. Soc. (1959) 2272; J. Chem. Soc. 84 (1962) 1876; J. Org. Chem. 35, (1970) 3149; J. Org. Chem. 36, (1971.) 3843 and Phosphorus, Sulfur and Silicon 42, (1989) 73.

In the EP-patent application 356 866 optionally halogen substituted methylenebisphosphonic acid esters and amide esters are described, which have a cholesterol biosynthesis inhibiting activity.

According to the invention it has been discovered that the novel partial amides and partial ester amides of methylenebisphosphonic acids and their salts in many cases exhibit more favourable properties than the corresponding bisphosphonic acids and salts due to their better kinetics and availability, their ability to participate as complex formers in the regulation of the metabolism of the organism being maintained.

They are well suited for the treatment of disorders relating to the metabolism of calcium and of other, especially bivalent metals. They may be used both for the treatment of diseases in the skeletal system, especially of bone formation and resorption disorders, such as of osteoporosis and. Paget's disease, as well as for the treatment of diseases in the soft tissues, such as of deposition and mineralisation conditions and bone formation disorders.

On the other hand, being pyrophosphate analogs, the new substituted methylenebisphosphonic acid derivatives are also suitable for the treatment of disorders in the (pyro)phosphate functions of the organism, including those functions, wherein an active, but disturbance-prone or wrongly functioning organic part is coupled to (pyro)phosphate or acts as a metal complex or a combination of the last mentioned.

The novel bisphosphonates regulate either directly or over an indirect mechanism the quality and level of cations and/or pyrophosphate compounds .freely present in the body fluids as well as of that binding to, active in and liberated from the tissues. Thus they are able to regulate the cellular metabolism, growth and destruction. Consequently they are useful for the treatment of e.g. cancer of the bone and metastases thereof, ectopic calcifications, urolithiasis, rheumatoid arthritis, bone infections and bone degradation.

Typical for the novel substituted methylenebisphosphonates is a selective desired and controlled action, providing for a better therapeutic index.

The invention concerns novel methylenebisphosphonic acid derivatives of the general formula I

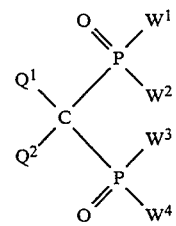

in which formula $W^1$, $W^2$, $W^3$ and $W^4$ are independently the group $OR^1$ or the group $NR^2R^3$ wherein $R^1$, $R^2$ and $R^3$ independently are hydrogen or straight or branched, optionally unsaturated $C_1$-$C^{22}$-alkyl, optionally substituted, optionally unsaturated $C_3$-$C_{10}$-cycloalkyl, aryl, aralkyl or silyl $SiR_3$, or the groups $R^2$ and $R^3$ form together with the adjacent nitrogen atom a 3 to 10-membered saturated, partly saturated or aromatic heterocyclic ring, wherein in addition to the nitrogen atom, there may be one or two heteroatoms from the group N, O and S, provided that in the formula I at least one of the groups $W^1$, $W^2$, $W^3$ and $W^4$ is hydroxy and at least one of the groups $W^1$, $W^2$, $W^3$ and $W^4$ is the amino group $NR^2R^3$, $Q^1$ and $Q^2$ are independently hydrogen, fluorine, chlorine, bromine or iodine, including the stereoisomers, such as the geometrical isomers and the optically active isomers, of the compounds, as well as the pharmacologically acceptable salts of the compounds.

Alkyl, alkenyl and alkynyl as the group $R^1$, $R^2$ and $R^3$ contain independently 1 to 22, respectively 2 to 22 carbon atoms, preferably 1 to 7, respectively 2 to 7, and advantageously 1 to 4, respectively 2 to 4 carbon atoms.

Cycloalkyl or -alkenyl as the group $R^1$, $R^2$, and $R^3$ contains 3 to 10 C-atoms, preferably 5 or 6 carbon atoms, and it may-unsubstituted or substituted for example with lower (1-4C) alkyl. Advantageously it is cyclopropyl, -butyl, -pentyl, -hexyl or -heptyl or the corresponding cycloalkenyl group.

Aryl or aralkyl as the group $R^1$, $R^2$ and $R^3$ means optionally $C_1$-$C_4$-lower alkyl, -lower alkoxy or halogen substituted monocyclic aryl or aralkyl, such as phenyl and benzyl, preferably, however, unsubstituted phenyl or benzyl. Halogen is chlorine, bromine, fluorine or iodine.

In the silyl group $SiR_3$ the group $R^3$ is lower alkyl containing 1 to 4 C-atoms, and is especially methyl, ethyl, isopropyt, butyl, t-butyl, or it is phenyl or $R^3$-substituted ted phenyl, whereby also different combinations of lower alkyls and phenyls come into question, such as dimethyl t-butyl, methyl diisopropyl, dimethyl phenyl, diethyl phenyl, methyl t-butyl phenyl, diisopropyl-(2,6-dimethyl phenyl).

When $R^2$ and $R^3$ together with the nitrogen atom form a heterocyclic, either saturated ring, this is typically for example morpholinyl, thiomorpholinyl, piperidinyl, piperazinyl, azetidinyl, aziridinyl, pyrrolidinyl, or a partly hydrogenated aromatic ring it is for example pyrrolyl, imidazolyl, triazolyl, tetrazolyl, oxazolyl, thiazolyl, pyridyl, pyrimidyl, pyrazinyl, pyridazinyl, azepinyl. This group can be substituted as has been mentioned earlier for cycloalkyl, but it is preferably, however, unsubstituted, such as pyrrolidinyl, morpholinyl or piperazinyl.

$Q^1$ and $Q^2$ are both preferably chlorine.

Salts of the compounds of the formula I are especially their salts with pharmaceutically acceptable bases, such as metal salts, for example Alkalimetal salts, especially litium, sodium and potassium salts, alkaline earth metal salts, such as calcium or magnesium salts, copper, aluminimum or zinc salts, as well as ammonium salts with ammonia or with primary, secondary and tertiary, both aliphatic and alicyclic as well as aromatic amines, and quaternary ammonium salts, such as halides, sulphates and hydroxides, salts with aminoalcohols, such as ethanol-, diethanol- and triethanolamines, tris(hydroxymethyl)aminomethane, 1- and 2-methyl- and 1,1-, 1,2- and 2,2-dimethylaminoethanols, N-mono- and N,N-dialkylaminoethanols, N-(hydroxymethyl- and ethyl)-N,N-ethanediamines, as well as amino crown ethers and cryptates, and heterocyclic ammonium salts, such as azetidinium, pyrrolidinium, piperidinium, piperazinium, morpholinium, pyrrolium, imidazolium, pyridinium, pyrimidinium, quinolinium, etc., salts.

Examples of preferred compounds of the invention are:

(Dichloromethylene) bisphosphonic acid P, P, P'-tris (diethyl amide)

(dichloromethylene) bisphosphonic acid P-monoisopropyl ester P-mono (diethylamide), (dichloromethylene) bisphosphonic acid P,P-bis(diethylamide)

(dichloromethylene)bisphosphonic acid mono(diethylamide)

(dichloromethylene) bisphosphonic acid mono(phenyl-N-methyl amide)

(dichloromethylene)bisphosphonic acid mono(benzylamide)

(dichloromethylene) bisphosphonic acid P, P'-bis (diethylamide).

The invention concerns also a process for the preparation of the compounds of the formula I, according to which a) in a compound of the formula

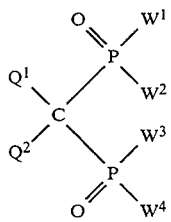

I' in which formula $Q^1$ and $Q^2$ have the same meaning as above and $W^1$, $W^2$, $W^3$ and $W^4$ have the same meaning as above, except hydroxy, at least one ester group $OR^1$ and/or amino group $NR^2R^3$ is hydrolysed to a free hydroxy group, in order to prepare a partial amide or partial ester amide derivative of the formula I, or b) in a methylenebisphosphonic acid tetraacid or its partial ester of the formula

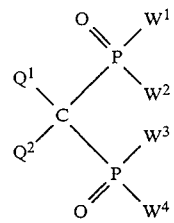

I'' which optionally is in acid chloride form, and wherein $Q^1$ and $Q^2$ have the same meaning as above, the groups $W^1$ to $W^4$ mean the group $OR^1$, wherein at least one of the groups $R^1$ is hydrogen, and the remaining groups $R^1$ have the same meaning as above, when in the compound I'' there is one hydroxy group, at least one ester group $OR^1$ is converted to an amide group, and when in the compound I'' there are more than one hydroxy group, a free hydroxy group is amidated with a suitable amine $NHR^2R^3$ and/or an ester group is converted to an amide group in order to prepare a partial amide or partial ester amide of the formula I, having at least one hydroxy group and at least one amine group, or c) a phosphonate having the formula

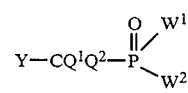

IX is reacted with an activated phosphate or a hydrogen phosphonate corresponding to the formula X

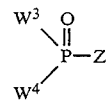

X wherein in the formulas; Y is hydrogen, hydroxy or halogen or other leaving group, Z is hydrogen, halogen, acyloxy, sulphonyloxy, alkoxy or aryloxy, and $W^1$ to $W^4$ and $Q^1$ and $Q^2$ have the same meaning as above, or is reacted with a phosphite corresponding to the formula X, or d) a bisphosphonite compound having the formula

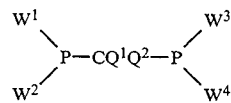

wherein $W^1$ to $W^4$ and $Q^1$ and $Q^2$ have the same meaning as above, or the corresponding hydrogen phosphonate compound, is oxidized to a compound of the formula I, and/or if desired, a compound of the formula I obtained, wherein $Q^1$ and/or $Q^2$ are hydrogen, is converted to a compound of the formula I, wherein $Q^1$ and/or $Q^2$ are halogen, and/or a compound of the formula I obtained, wherein $Q^1$ and/or $Q^2$ are halogen, is mono- or di-dehalogenated to a compound of the formula I, wherein $Q^1$ and/or $Q^2$ are hydrogen, and/or, if desired, a compound of the formula I obtained is converted to another compound according to the formula I by esterification, transesterification, amidation or transamidation and/or, if desired, a partial amide or partial ester amide acid obtained is converted to a salt or an obtained salt is converted to the free acid.

Thus according to one process the compounds are prepared by selective hydrolysis of the ester or amide groups of the tetra(amide ester)compounds corresponding to the formula I. Thus a compound is used as the starting material, wherein $Q^1$ and $Q^2$ have the same meaning as above and the groups $W^1$ to $W^4$ have the same meaning as in the formula I, except hydroxy, and at least one of the groups $W^1$ to $W^4$ is the amino group $NR^2R^3$ and of the ester or amide groups contained in the compound at least one is hydrolyzed to the free hydroxy group, or several so that at least one amide group remains.

The progress of hydrolysis may be followed for example chromatographically or by using $^{31}$P-NMR-spectroscopy. The reaction may be interrupted when the concentration of a desired partial (ester) amide is at its greatest and the product may be isolated from the reaction mixture either as the free acid or a salt by precipitation, extraction or chromatographically, and a salt form may be converted into the free acid -or a free acid may be converted into its salt.

The compounds according to this invention may also be prepared by selective esterification and amidation of bisphosphonic acids. A tetraacid ($W^1$ to $W^4$=OH) may thus used as a starting material, which can be the free acid or a salt, such as a metal or ammonium salt, or the corresponding bisphosphonic acid tetrachloride, and a suitable amine $NHR^2R^3$. Similarly, a suitable partial ester acid, partial amide acid or partial ester amide acid or a salt thereof or the corresponding acid chloride may be used. The ester group may be exchanged to an amide group over the acid halide or directly using known methods.

Partial amides and ester amides according to the invention may also be prepared by constructing the P-C-P frame from its parts

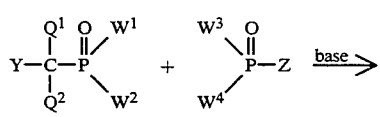

wherein in the formula Y is hydrogen, hydroxy or halogen or other leaving group, Z is halogen, acyloxy, sulphonyloxy, alkoxy or aryloxy, and $W^1$ to $W^4$ and $Q^1$ and $Q^2$ have the meaning given above. As the base, for example, sodium hydride, butyl litium or litium diisopropylamide may be used. In the starting material optionally present free acid sites and/or amine hydrogens (one of the groups $R^1$ to $R^3$=H) have to be neutralized, by using a sufficient amount of base, prior to the coupling reaction.

Also the Michaelis-Arbuzov reaction may be used, whereby the second reacting compound is a phosphite, or the Michaelis-Becker reaction, whereby Z is hydrogen.

The amides and ester amides according to the invention may also be prepared from P-C-P-structures at a lower oxidation level by oxidation

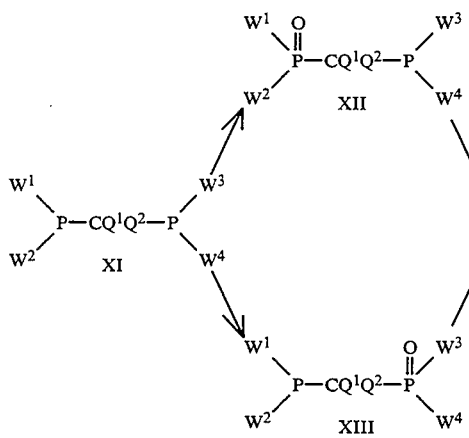

whereby in the formulas $W^1$ to $W^4$ and $Q^1$ and $Q^2$ have the meaning given above, and whereby the phosphonite structure may exist in an equilibrium with the hydrogenphosphonate structure. All conventional oxidation agents, or their solutions, such as hydrogen peroxide, perhalogen compounds, peracids, permanganate etc., come into question as oxidating agents.

The compounds according to the invention may also be prepared by halogenating corresponding compounds, wherein one or both of the groups $Q^1$ and $Q^2$ are hydrogen, or exchange the halogen(s) for another, or remove one or both:

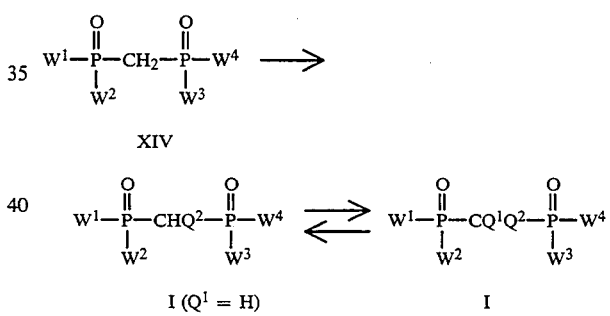

In the formulas $W^1$ to $W^4$ and $Q^1$ and $Q^2$ are the same as before. Halogenation takes place as is described later.

Partial amides and ester amides of bisphosphonic acids according to the invention may also be prepared from other partial amides or ester amides by performing an intra- or intermolecular exchange reaction.

The tetra(ester)amides and corresponding tetraacids used as starting materials in the above reactions may be prepared by processes known as such from literature by constructing the P-C-P frame from its parts, for example using the above mentioned Michaelis-Becker-, Michaelis- Arbuzov- or carbanion reaction.

The compounds prepared may, if necessary, be converted into other suitable compounds by using exchange reactions taking into account the preparation of a desired partial (ester)amide. Thereby the amide groups and ester groups $W^1$ to $W^4$ may be converted directly or over the corresponding phosphonochloride or by using other known methods.

Halogen atoms(s) may be introduced in place of the hydrogens on the carbon between the phosphorus atoms of the bisphosphonates also in the form of tetra(ester)amides, whereby the reaction advantageously takes place with hypohalite. Also conventional halogenation reactions come into question, such as the reactions of bisphosphonic carbanions prepared with a strong base with elemental halogens or halogenations with N-haloamines and other active halides or polyhalogen compounds.

The halogen substituents of the carbon may also be introduced in the bisphosphonate structure as a halogenated monophosphonate IX, whereby $Q^1$ and/or $Q^2$ are halogens. A halogen in a carbon of the frame may also be exchanged to hydrogen, often by nucleophilic dehalogenation, or to another halogen using known reactions. Mixed halogen compounds may also be prepared applying the above mentioned halogenation and exchange reactions stepwise (cf Phosphorus and Sulfur, 37 (1988) 1).

Optically active partial amides and partial ester amides may be prepared best by using known optically active compounds, such as optically active alcohols, in the preparation of the above mentioned starting materials, intermediates and end products, or in the exchange reactions.

The properties of the compounds according to the invention have been tested in the following test system.

The parathyroid hormone stimulated bone resorption inhibition activity of the compounds in vitro in mouse calvaria was determined (Reynolds & Dingle (Calc Tiss Res 1970; 4:339).

TABLE 2

| Antiresorptive activity Inhibition of resorption (%) | |
|---|---|
| | 100 μM |
| Clodronate (dichloromethylene)bisphosphonic acid | 43 |
| mono(diethylamide) (dichloromethylene)bisphosphonic acid | 43 |
| P,P'-bis(diethylamide) (dichloromethylene)bisphosphonic acid | 38 |
| tris(diethylamide) (dichloromethylene)bisphosphonic acid | 44 |
| P-monoisopropyl ester P-mono(diethylamide) | 44 |

From the table the superior relative in vitro activity of the compounds of the invention are evident when taking into account that they bind only to a limited degree to hydroxyapatite and partly inhibit crystal growth. They provide for a better therapeutic index, exhibiting lesser side effects.

The partial amides and partial ester amides of substituted bisphosphonic acids of the formula I may be used as pharmaceuticals as such, or as their pharmacologically suitable salts, such as the alkali or ammonium salts. Such salts may be prepared by reacting the (ester)amide acids with the corresponding inorganic or organic bases. Depending on the reaction conditions, the amide or ester amide salts may also be formed directly in the above mentioned reactions.

The new compounds I according to this invention may be administered enterally or parenterally. All conventional administration forms, such as tablets, capsules, granules, syrups, solutions, implants and suspensions come into question. Also all adjuvants for manufacture, dissolution and administration of the preparation, as well as stabilizers, viscosity regulating and dispersion agents and buffers, may be used.

Such adjuvants include i.a. tartrate and citrate buffers, alcohols, EDTA and other nontoxic complexing agents, solid and liquid polymers and other sterile substrates, starch, lactose, mannite, methylcellulose, talc, silicic acids, fatty acids, gelatine, agar-agar, calcium phosphate, magnesium stearate, animal, and vegetable fats and, if desired, flavouring and sweetening agents.

The dosage depends on several factors, for example on the manner of administration, species, age and individual condition. The daily doses are about 1 to 1000 mg, usually 10 to 200 mg per person, and they may be administered as a single dose or may be divided into several doses.

In the following, examples of a typical capsule and a tablet are given:

| | mg/caps. |
|---|---|
| Capsule | |
| Active ingredient | 100.0 mg |
| Starch | 20.0 mg |
| Magnesium stearate | 1.0 mg |
| Tablet | |
| Active ingredient | 400.0 mg |
| Microcrystalline cellulose | 20.0 mg |
| Lactose | 67.0 mg |
| Starch | 10.0 mg |
| Talc | 4.0 mg |
| Magnesium stearate | 1.0 mg |

For medicinal use, also an intramuscularly or parenterally administered preparation may be made, for example an infusion concentrate, wherein as adjuvants e.g. sterile water, phosphate buffer, NaCl, NaOH or HCl or other known pharmaceutical adjuvants suitable for the purpose may be used.

The compounds in amide and ester amide acid form according to the invention are liquid or waxy substances, usually soluble in organic solvents and in some instances in water. Their salts are solid, crystalline or typically powdery substances which-usually dissolve well in water, in some instances in organic solvents, but only some structure types being poorly soluble in all solvents. The compounds are very stable, also in their neutral solutions at room temperature.

The structure of the compounds may easily be verified with $^1$H-, $^{13}$C- and $^{31}$P-NMR-spectroscopy and FAB-masspectrometry, or when silylated, with EI-masspectrometry. For concentration and impurity determinations 31P-NMR-spectroscopy is very suitable. Also for polar compounds as such ion exchange and exclusion-HPLC may be used and for tetra(ester)amides and corresponding silylated derivatives GLC or GC/MS may be used. From the compounds nitrogen, sodium and other metals were determined separately as well as the possible crystal water content.

The following examples illustrate the invention without limiting the same in any way.

EXAMPLE 1

(Dichloromethylene) bisphosphonic acid P', P'-bis (diethylamide) and its disodium salt 3.83 g ( 0.01 moles) of (dichloromethylene)bisphosphonic acid P,P-dimethyl ester P',P'-bis(diethylamide) is dissolved in 20 ml of anhydrous methylene chloride and 3.06 g (0.02 moles) of bromotrimethylsilane is added while stirring as well as 3.00 g (0.02 moles) of sodium iodide and the mixture is stirred for 6 hours at room temperature (the progress of the reaction is followed by NMR). The solvent is evaporated) in vacuum and the residue dissolved in anhydrous ether. The mixture is filtered and the filtrate is evaporated to constant weight under vacuum, whereby (dichloromethylene)-bisphosphonic acid P,P-bis(trimethylsilyl ester) P',P'-bis(diethylamide) is obtained in a quantitaive yield as a brown oil. The evaporation residue is dissolved in 30 ml of methanol and the solution stirred for 5 min at room temperature and evaporated to a constant weight under vacuum, whereby (dichloromethylene)bisphosphonic acid P',P'-bis(diethylamide) is obtained as a brown, thick-flowing oil. This is dissolved in 35 ml of methanol-acetone (1:1) and to the solution 3 ml of a 5N NaOH solution is added while stirring and cooling. The solution is evaporated under vacuum and to the residue acetone is added and the mixture is stirred. The precipitate is filtered and washed with acetone and air-dried. Yield is appr. 2.8 g (70% of theor.) of colourless, crystalline (dichloromethylene)bisphosphonic acid P',P'-bis(diethyl amide) disodium salt ($^{31}$P-NMR (D$_2$O): $\delta$8.60 ppm (P), 32.16 ppm (P'), $^2J_{PP}$=15.6 Hz, $^3J_{PH}$=9.2 Hz), the concentration of which is >90%.

I.a. the following bisphosphonic acid amides and ester amides as well as their sodium salts may be prepared in an analogous manner:

From P'-ethyl P-methyl P,P'-bis(diethylamido) (dichloromethylene) bisphosphonate over P,P'-bis(trimethylsilyl) P,P'bis (diethylamido) (dichloromethylene)-bisphosphonate:

P,P'-bis(diethylamido) (dichloromethylene) bisphosphonate (cf. Example 6) ($^{31}$P-NMR (CDCl$_3$): $\delta$15.66 ppm) which can be converted to its disodium salt as has been described above ($^{31}$P-NMR (D$_2$O): $\delta$13.94 ppm).

From P'-ethyl P,P-dimethyl P'-morpholino(dichloromethylene)bisphosphonate (see Example 4) over P,P,P'-tris(trimethylsilyl) P'-morpholino(dichloromethylene)bisphosphonate:

P'-morpholino (dichloromethylene)bisphosphonate ($^{31}$P-NMR (D$_2$O): $\delta$6.02 (P), 18.06 (P'), $^2J_{PP}$ 17.6 Hz) and trisodium salt ($^{31}$P-NMR (D$_2$O): $\delta$9.44 ppm (P), 10.75 ppm (P'), $^2J_{PP}$=18.1 Hz).

From P,P,P'-trimethyl P'-dibutylamido (dichloromethylene)bisphosphonate (see Example 4) over P,P,P'-tris (trimethylsilyl) P'- (dibutylamido) (dichloromethylene) bisphosphonate:

P'- (dibutylamido) (dichloromethylene) bisphosphonate ( trisodium salt, $^{31}$P-NMR (D$_2$O): $\delta$9.58 ppm (P), 12.58 ppm (P'), $^2J_{PP}$=15.2 Hz).

From P-methyl P'-butylamido(dichloromethylene) bisphosphonate (see Example 6) (or P,P,P'-trimethyl P'-(butylamido) (dichloromethylene)bisphosphonate) over P,P,P'-tris(trimethylsilyl) P'-(butylamido) (dichloromethylene) bisphosphonate:

P'-(butylamido) (dichloromethylene) bisphosphonate ($^{31}$P-NMR (D$_2$O): $\delta$7.11 ppm (P), 9.49 ppm (P'), $^2J_{PP}$=21.0 Hz).

From P-ethyl P,P'-dimethyl P'-(dioctylamido) (dichloromethylene)bisphosphonate (see Example 4) over P,P,P'-tris(trimethylsilyl) P'- (dioctylamido) (dichloromethylene)-bisphosphonate ($^{31}$P-NMR (CDCl$_3$): $\delta$−7.16 ppm (P), 6.28 pm (P'), $^2J_{PP}$=27.2 Hz):

P'-(dioctylamido) (dichloromethylene) bisphosphonate ($^{31}$P-NMR (CDCl$_3$): $\delta$9.78 ppm (P), 15.41 ppm (P') $^2J_{PP}$=23.2 Hz) and trisodium salt ($^{31}$P-NMR (D$_2$O): $\delta$12.23 ppm (P), 18.01 ppm (P') $^2J_{PP}$=22.0 Hz).

From P'-ethyl P,P-dimethyl P'-(benzylmethylamido)(dichloromethylene) bisphosphonate ( see Example 4 ) over P,P,P'-tris(trimethylsilyl) P'-(benzylmethylamido) (dichloromethylene)bisphosphonate:

P'-(benzylmethylamido) (dichloromethylene) bisphosphonate ($^{31}$P-NMR (D$_2$O): $\delta$10.32 ppm (P), 15.60 ppm (P'), $^2J_{PP}$=14.9 Hz).

From P'-ethyl P,P-dimethyl P'-(benzylmethylamido)(chloromethylene)bisphosphonate (see Example 10) over P,P,P'-tris(trimethylsilyl) P'-(benzylmethylamido)(chloromethylene)bisphosphonate:

P'-(benzylmethylamido)(chloromethylene)bisphosphonate.

From P,P,P'-trimethyl P'-(diethylamido) (chloromethylene) bisphosphonate (see Example 10) over P,P,P'-tris(trimethylsilyl) P'-(diethylamido) (chloromethylene) bisphosphonate:

P'-(diethylamido) (chloromethylene) bisphosphonate (trisodium salt, $^{31}$P-NMR (D$_2$O): $\delta$9.61 ppm (P), 17.84 ppm (P'), $^2J_{PP}$=2.9 Hz).

From P,P-dimethyl P',P'-bis(diethylamido) (chloromethylene)bisphosphonate (see Example 10) over P,P-bis(trimethylsilyl) P', P'-bis (diethylamido) (chloromethylene) bisphosphonate:

P', P'-bis (diethylamido) (chloromethylene) bisphosphonate (disodium salt; $^{31}$P-NMR (D$_2$O): $\delta$7.94 ppm (P), 34.17 ppm (P'), $^2J_{PP}$=3.1 Hz, $^2_{PP}$=16.7 Hz) P,P-dimethyl P',P'-bis(diethylamido)(dichloromethylene)bisphosphonate used as the starting material above may be prepared in the following manner:

Step 1

Into a THF-hexane solution of LDA (litium diisopropylamide), which contains 0.10 moles of LDA, 10.31 g (0.05 moles) of methyl phosphonic acid bis (diethylamide) ($^{31}$P-NMR (CDCl$_3$): $\delta$34.63 ppm) (prepared from methane phosphonic acid dichloride and diethyl amine) in 20 ml anhydrous THF is added while stirring under a N$_2$-atmosphere at −75° −78° C. After the addition,, the mixture is stirred for 15 min, whereafter 7.22 g (0.05 moles) of chlorophosphonic acid dimethyl ester is added in 10 ml of anhydrous THF and stirring is continued for an additional 15 min at −75°-−78° C. The temperature of the mixture is raised to about −50° C. and pH is adjusted to about 5-6 with 5N HCl. The mixture is heated to room temperature and the solvents are distilled under vacuum. The residue is extracted with 3×70 ml of CHCl$_3$ and the combined extracts are washed with a 10% NaHCO$_3$-solution and water and is dried (MgSO$_4$) and filtered. The filtrate is evaporated under vacuum, whereby appr. 15.7 g (100% of theor) of P,P-dipethyl P',P'-bis(diethylamido)methylenebisphosphonate is obtained as a light yellow oil ($^{31}$P-NMR (CDCl$_3$): $\delta$25.43 ppm (P), 25.51 ppm (P'), $^2J_{PP}$=4.5 Hz), the concentration of which is 98%.

I.a. the following symmetrical and unsymmetrical methylenebisphosphonic acid ester amides can be prepared in an analogous manner:

From methyl(diethylamido)methylphosphonate ($^{31}$P-NMR (CDCl$_3$): $\delta$34.56 ppm) and dimethylchlorophosphonate P,P,P'-trimethyl P'-(diethylamido) methylenebisphosphonate ($^{31}$P-NMR (CDCl$_3$): $\delta$23.89 ppm (P.) 25.11 ppm (P'), $^2J_{PP}$=5.4 Hz).

From methyl (diethylamido) methylphosphonate and ethyl (diethylamido)chlorophosphonate ($^{31}$P-NMR (CDCl$_3$): $\delta$16.51 ppm) P'-ethyl P-methyl P,P'-bis (diethylamido) methylenebisphonate ($^{31}$P-NMR (CDCl$_3$): $\delta$26.69/26.66 ppm (P'), 24.78/24.91 ppm (P), $^2J_{PP}$=7.7/1.9 Hz).

From isopropyl (diethylamido) methylphosphonate ($^{31}$P-NMR (CDCl$_3$): $\delta$27.67 ppm) and dimethylchlorophosphonate P,P-dimethyl P'-isopropyl P'-(diethylamido) methylenebisphosphonate ($^{31}$P-NMR (CDCl$_3$): δ22.10 ppm (P), 24.38 ppm (P'), $^2J_{PP}$=5.8 Hz).

From dimethylmethylphosphonate and ethylmorpholinochlorophosphonate ($^{31}$P-NMR (CDCl$_3$): δ14.16 ppm) P'-ethyl P,P-dimethyl P'-morpholinomethyienebisphosphonate ($^{31}$P-NMR (CDCl$_3$): δ21.43 ppm (P), 23.39 ppm (P'), $^2J_{PP}$=3.4 Hz)

From methyl (dibutylamido) methylphosphonate ($^{31}$P-NMR (-CDCl$_3$): δ35.94 ppm) and dimethylchlorophosphonate P,P,P'-trimethyl P'-(dibutylamido) methylenebisphosphonate ($^{31}$P-NMR (CDCl$_3$): δ24.11 ppm (P), 25.30 ppm (P') $^2J_{PP}$=6.1 Hz).

From dimethylmethylphosphonate and ethyl (dioctylamido) chlorophosphonate ($^{31}$P-NMR (CDCl$_3$): δ17.23 ppm) P'-ethyl P,P-dimethyl P'-(dioctylamido) methylenebisphosphonate ($^{31}$P-NMR (CDCl$_3$): δ23.70 ppm (P), 24.39 ppm (P'), $^2J_{PP}$=6.4 Hz).

From bis (diethylamido) methylphosphonate ($^{31}$P-NMR (CDCl$_3$): δ34.63 ppm) and ethyl (diethylamido) chlorophosphonate ($^{31}$P-NMR (CDCl$_3$): δ16.51 ppm) P-ethyl P,P'P'-tris(diethylamido)methylenebisphosphonate ($^{31}$P-NMR (CDCl$_3$): δ27.13 ppm (P), 27.35 ppm (P'), $^2J_{PP}$=3.9 Hz ).

From dimethylmethylphosphonate and ethyl(benzylmethylamido) chlorophosphonate ($^{31}$P-NMR (CDCl$_3$): δ17.69 ppm) P'-ethyl P,P-dimethyl P'-(benzylmethylamido) methylenebisphosphonate ($^{31}$P-NMR (CDCl$_3$): δ24.19 ppm (P), 24.29 ppm (P'), $^2J_{PP}$=3.0 Hz)

From diethylmethylphosphonate and ethylpiperidinochlorophosphonate ($^{31}$P-NMR (CDCl$_3$): ) P,P,P'-triethyl P'-piperidinomethylenebisphosphonate.

From dimethylmethylphosphonate and methyl (diallylamido) chlorophosphonate ($^{31}$P-NMR (CDCl$_3$): δ16.18 ppm P,P,P'-trimethyl P'-(diallylamido) methylenebisphosphonate.

From dimethylmethylphosphonate and ethyl(N-methylpiperazino) chlorophosphonate ($^{31}$P-NMR (CDCl$_3$): δ14.84 ) P'-ethyl P,P-dimethyl P'-(N-methylpiperazino)methylenebisphosphonate ($^{31}$P-NMR (CDCl$_3$): δ21.72 ppm (P), 23.92 ppm (P') $^2J_{pp}$=3.4 Hz).

Step 2

15.7 g (0.05 moles) of the evaporation residue of methylenebisphosphonic acid P,P-dimethyl ester P',P'-bis(diethylamide) obtained in Step 1 is dissolved in 200 ml of CCl$_4$ and 200 ml of a 10% NaOCl-solution and 10 g of benzyl triethyl ammonium chloride is added. The mixture is stirred for 45 min at room temperature (the progress of the reaction is followed by NMR) and the organic phase is separated and washed with water and dried (Na$_2$SO$_4$) and filtered. The filtrate is evaporated under vacuum, whereby appr. 15.3 g (80% of theor.) of (dichloromethylene)bisphosphonic acid P,P-dimethyl ester P',P'-bis(diethylamide) is obtained as a light yellow oil ($^{31}$P-NMR (CDCl$_3$): δ12.91 ppm (P), 25.31 ppm (P'), $^2J_{PP}$=22.7 Hz) the concentration of which is 97%.

I.a. the following symmetrical and unsymmetrical (dichloromethylene)bisphosphonic acid ester amides can be prepared in an analogous manner:

From P-ethyl P'-methyl P,P'-bis (diethylamido) methylenebisphosphonate: P-ethyl P'-methyl P,P'-bis(diethylamido) (dichloromethylene) bisphosphonate ($^{31}$P-NMR (CDCl$_3$): δ16.39/16.48 ppm (P), 18.60/18 36 ppm (P'), $^2J_{PP}$=20.5/17.9 Hz).

From P-ethyl P,P',P'-tris (diethylamido) methylenebisphosphonate: P-ethyl P,P', P'-tris (diethylamido) (dichloromethylene) bisphosphonate ($^{31}$P-NMR (CDCl$_3$): δ17.66 ppm (P), 26.54 ppm (P'), $^2J_{PP}$=20.7 Hz).

EXAMPLE 2

(Dichloromethylene) bisphosphonic acid tris (diethylamide) and its piperidinium salt 4.4 g (0.01 moles) of (dichloromethylene)bisphosphonic acid P-ethyl ester P,P',P'-tri(diethylamide) (see Example 1) is stirred in 22 ml of piperidine for 1 h at appr. 100° C. and the excess piperidine is evaporated under vacuum. The residue is stirred while cooling into 15 ml of anhydrous ether and the precipitate filtered and air-dried. Yield is appr. 4.2 g (85% of theor.) of colourless, crystalline (dichloromethylene) bisphosphonic acid tris (diethylamide) piperidinium salt ($^{31}$P-NMR (CDCl$_3$): δ12.26 ppm (P), 30.19 ppm (P'), $^2J_{PP}$=16.5 Hz), the concentration of which is 99% and from which the corresponding acid can be liberated with acid treatment.

In the same manner (dichloromethylene)bisphosphonic acid tris (diethylamide)-(N-ethylpyridinium salt) ($^{31}$P-NMR (CDCl$_3$): δ10.23 ppm (P), 29.51 ppm (P'), $^2J_{PP}$=17.7 Hz) has been prepared using pyridine treatment.

EXAMPLE 3

P'-Morpholino (dichloromethylene) bisphosphonic acid ethyl ester 1.85 g (0.005 moles) of P'-morpholino(dichloromethylene)bisphosphonic acid P'-ethyl P,P-dimethyl ester (see Example 4) and 1.84 g (0.012 moles) of trimethylsilyl bromide in 30 ml of anhydrous CH$_2$Cl$_2$ is stirred under reflux for 30 min and evaporated under vacuum. The residue is dissolved in 30 ml of anhydrous CH$_3$OH and Stirred for 15 min at room temperature and evaporated under vacuum, whereby appr. 1.7 g (80% of theor.) of P'-morpholino(dichloromethylene)bisphosphonic acid P'-ethyl ester is obtained ($^{31}$P-NMR (CDCl$_3$): δ8.29 ppm (P), 13.39 ppm (P'), $^2J_{PP}$=22.6 Hz) as a yellow oil at a concentration of >85%.

EXAMPLE 4

Dichloromethylene)bisphosphonic acid (mono)diethylamide and its trisodium salt 5.5 g (0.02 moles) of methylenebisphosphonic acid P,P,P'-trimethyl ester P'-diethylamide (see Example 1) is added at 0° C. while stirring to a mixture containing 26 g NaHCO$_3$, 68 ml of a 10% NaOCl-solution and 30 g of ice, whereafter the mixture is stirred for 1.5 hours at 0° C. and 2.5 hours at room temperature (the progress of the reaction is followed with NMR). The mixture is filtered and the filtrate extracted with toluene. The combined toluene extracts are washed with a 10% NaHCO$_3$-solution and dried (Na$_2$SO$_3$) and filtered. The filtrate is evaporated under vacuum, whereby appr., 5.8 g (85% of theor.) of (dichloromethylene)bisphosphonic acid P,P,P'-trimethyl ester P'-diethylamide is obtained ($^{31}$P-NMR (CDCl$_3$): δ12.02 ppm (P), 17.09 ppm (P'), 17.09 ppm (P'), $^2J_{PP}$=21.4 Hz) as a colourless oil at a concentration of >97%.

The evaporation residue is hydrolysed to (dichloromethylene) bisphosphonic acid (mono) diethylamide ($^{31}$P-NMR (CDCl$_3$): δ10.00 ppm (P), 13.90 ppm (P'), $^2J_{PP}$=18.5 Hz) over (dichloromethylene) bisphosphonic acid P,P,P'-trimethylsilyl ester P'-diethylamide ($^{31}$P-NMR (CDCl$_3$): δ−9.10 ppm (P), 5.29 ppm (P'), $^2J_{PP}$=25.7 Hz ) in the manner described in the Example 1 at a yield of appr. 90%.

The product can be converted to the corresponding trisodium salt by treating an acetone solution of the material with three equivalents of a 5N NaOH-solution. The concentration of the trisodium salt crystallized from water-methanol ($^{31}$P-NMR (D$_2$O): δ10.23 ppm (P), 15.72 ppm (P'), $^2J_{PP}$=15.2 Hz) is >95%.

I.a. the following symmetrical and unsymmetrical (dichloromethylene)bisphosphonic acid ester amides can be prepared in an analogous manner:

From P,P-dimethyl P'-isopropyl P'-(diethylamido) methylenebisphosphonate (see Example 1) P,P-dimethyl P'-isopropyl P'-(diethylamido) (dichloromethylene) bisphosphonate ($^{31}$P-NMR (CDCl$_3$): δ12.13 ppm (P), 13.50 ppm (P') $^2J_{PP}$=22.8 Hz).

From P'-ethyl P,P-dimethyl P'-morpholinomethylenebisphosphonate (see Example 1) P'-ethyl P,P-dimethyl P'-morpholino(dichloromethylene)bisphosphonate ($^{31}$P-NMR (CDCl$_3$): δ11.68 ppm (P), 12.26 ppm (P'), $^2J_{PP}$=22.4 Hz).

From P,P,P'-trimethyl P'- (dibutylamido) methylenebisphosphonate (see Example 1) P,P,P'-trimethyl P- (dibutylamido) (dichloromethylene)bisphosphonate ($^{31}$P-NMR (CDCl$_3$): δ11.88 ppm (P), 16.78 ppm (P'), 21.3 Hz).

From P'-ethyl P,P-dimethyl P'-(dioctylamido) methylenebisphosphonate (see Example 1) P'-ethyl P,P-dimethyl P'(dioctylamido) (dichloromethylene) bisphosphonate ($^{31}$P-NMR (CDCl$_3$): δ11.93 ppm (P), 15.15 ppm (P'), $^2J_{PP}$=22.1 Hz)

From P'-ethyl P,P-dimethyl P'-(benzylmethylamido)methylenebisphosphonate (see Example 1) P'-ethyl P,P-dimethyl P'-(benzylmethylamido) (dichloromethylene) bisphosphonate ($^{31}$P-NMR (CDCl$_3$): δ11.70 ppm. (P), 15.01 ppm (P'), $^2J_{PP}$=23.0 Hz) .

From P'-ethyl P,P-dimethyl P'-(methylamido) methylenebisphosphonate (see Example 9) P'-ethyl P,P-dimethyl P'(methylamido) (dichloromethylene) bisphosphonate ($^{31}$P-NMR (CDCl$_3$): δ13.26 ppm (P), 10.75 ppm (P), $^2J_{PP}$=23.0 Hz)

From P,P,P'-trimethyl P'-(butylamido)methylenebisphosphonate P,P,P'-trimethyl P'-(butylamido)(dichloromethylene)bisphosphonate.

From P,P,P'-trimethyl P'-piperidinomethylenebisphosphonate (see Example 1) P,P,P'-trimethyl P'-piperidino(dichloromethylene) bisphosphonate.

From P,P,P'-triethyl P'-(diallylamido)methylenebisphosphonate (see Example 1) P,P,P'-triethyl P'-diallylamido(dichloromethylene)bisphosphonate.

EXAMPLE 5

(Dichloromethylene)bisphosphonic acid tetrakis (diethylamide)

Into 10.0 g (0.04 moles) of methylenebisphosphonic acid tetrachloride (prepared from tetraisopropylmethylenebisphosphonate and phosphorus pentachloride) in 60 ml of anhydrous toluene 23.4 g (0.32 moles) of diethylamine is added at <50° C. within appr. 30 min in 40 ml of anhydrous toluene, whereafter the mixture is stirred for 1 hour at appr. 50° C. and the mixture is cooled and filtered. The filtrate is evaporated under vacuum, whereby appr. 12.6 g (80% of theor.) of methylenebisphosphonic acid tetrakis(diethylamide) is obtained ($^{31}$P-NMR (CDCl$_3$): δ27.78 ppm) as a light yellow oil at a concentration of >85%.

The evaporation residue (8.0 g=0.02 moles) is chlorinated as has been described in the Example 1 (stirring for 72 h at room temperature), whereby appr. 7.5 g (80% of theor. ) of (dichloromethylene)bisphosphonic acid tetrakis(diethylamide) ($^{31}$P-NMR (CDCl$_3$): δ26.29 ppm) is obtained as a light yellow oil, at a concentration of >90%.

I.a. the following methylene and (dichloromethylene)bisphosphonic acid tetrakisamides can be prepared in an analogous manner from methylenebisphosphonic acid tetrachloride:

Tetrakis (dioctylamido) (dichloromethylene) bisphosphonate ($^{31}$P-NMR (CDCl$_3$): δ26.50 ppm) over tetrakis(dioctylamido)methylenebisphosphonate ($^{31}$P-NMR (CDCl$_3$): δ28.00 ppm) .

EXAMPLE 6

P'-Morpholino (dichloromethylene) bisphosphonic acid methyl ester and its dimorpholinium salt 18.5 g (0.05 moles) of P'-morpholino(dichloromethylene)bisphosphonic acid P'-ethyl P,P-dimethyl ester (see Example 4) in 70 ml of piperidine is mixed for 20 min at appr. 100° C. and the mixture is evaporated under vacuum. The residue is stirred into anhydrous ether and the precipitate separated by filtering and is washed with ether and dried to constant weight. The yield is appr. 20 g (80% of theor.) of colourless crystalline P'-morpholino(dichloromethylene)bisphosphonic acid P-methyl ester dipiperidinium salt ($^{31}$P-NMR (D$_2$O): δ0.82 ppm (P), 9.70 ppm (P'), $^2J_{PP}$=15.4 Hz) at a concentration of >97% and wherefrom the corresponding free bisphosphonic acid ($^{31}$P-NMR (CDCl$_3$): ) can be liberated with acid treatment.

I.a. the following symmetrical (dichloromethylene)-bisphosphonic acid ester amides can be prepared in an analogous manner:

From P,P,P'-trimethyl P'-(diethylamido) (dichloromethylene)bisphosphonate (see Example 4) P-methyl P'-(diethylamido) (dichloromethylene) bisphosphonate (dimorpholinium salt, $^{31}$P-NMR (D$_2$O): δ11.10 ppm (P), 12.76 ppm (P') $^2J_{PP}$=15.3 Hz).

From P,P,P'-trimethyl P'-(dibutylamido) (dichloromethylene)bisphosphonate (see Example 4) P-methyl P'-(dibutylamido) (dichloromethylene-) bisphosphonate (disodium salt, $^{31}$P-NMR (D$_2$O): δ11.16 ppm (P), 12.88 ppm (P') $^2J_{PP}$=16.2 Hz).

From P,P,P'-trimethyl P'-piperidino(dichloromethylene)bisphosphonate (see Example 4) P-methyl P'-piperidino(dichloromethylene)bisphosphonate (dipiperidinium salt, ($^{31}$P-NMR (D$_2$O): δ10.90 (P), 10.41 (P'), $^2J_{PP}$=15.3 Hz)

From P,P,P'-triethyl P'-(diallylamido) (dichloromethylene) bisphosphonate (see Example 4) P-ethyl P'-(diallyl) (dichloromethylene) bisphosphonate (disodium salt, $^{31}$P-NMR (D$_2$O): δ9.98 ppm (P), 12.48 ppm (P') $^2J_{PP}$=15.6 Hz)

From P,P,P'-trimethyl P'-(phenylamido) (dichloromethylene) bisphosphonate (see Example ) P-methyl P'-(phenylamido)(dichloromethylene) bisphosphonate (dianilinium salt, $^{31}$P-NMR (D$_2$O): δ10.25 ppm (P), 6.60 ppm (P'), ($^2J_{PP}$=17.3 Hz).

From P,P,P'-trimethyl P'-(phenylisopropylamido) (dichloromethylene)bisphosphonate (see Example ) P-methyl P'-(phenylisopropylamido) (dichloromethylene)bisphosphonate (bis (N-isopropylanilinium salt), $^{31}$P-NMR (D$_2$O): δ10.48 ppm (P), 6.74 ppm (P'), $^2J_{PP}$=17.3 Hz From P'-ethyl P,P-dimethyl P'-(benzylmethylamido) (dichloromethylene)bisphosphonate (see Example 4)

P-methyl P'-(benzylmethylamido) (dichloromethylene) bisphosphonate (dipiperidinium salt, $^{31}$P-NMR (D$_2$O): $\delta$10.86 ppm (P), 12.29 ppm (P'), $^2J_{PP}$=15.4 Hz)

From P,P,P'-trimethyl P'-(butylamido) (dichloromethylene)bisphosphonate (see Example ) P-methyl P'-(butylamido)(dichloromethylene)bisphosphonate ($^{31}$P-NMR (D$_2$O): $\delta$8.15 ppm (P), 9.30 ppm (P') $^2J_{PP}$=20.2 Hz)

From P'-ethyl P-methyl P,P'-bis (diethylamido) (dichloromethylene) bisphosphonate (see Example 1) P,P'-bis(diethylamido) (dichloromethylene) bisphosphonate (disodium salt, $^{31}$P-NMR (D$_2$O): $\delta$13.94 ppm). (Alternative preparation: see Example 1).

EXAMPLE 7

(Dichloromethylene) bisphosphonic acid P'-isopropyl ester P'-diethylamide and its disodium salt 7.4 g (0.02 moles) of (dichloromethylene)bisphosphonic acid P'-isopropyl P,P-dimethyl ester P'-diethylamide (see Example 4) is dissolved in 120 ml of anhydrous CH$_3$CN and while stirring and cooling 5.6 ml (0.04 moles) of anhydrous triethylamine as well as 20.3 ml (0.16 moles) of chlorotrimethylsilane is added. The mixture is stirred under reflux for 5 h and evaporated under vacuum, whereby appr. 9.7 g (100% of theor.) of almost colourless oily (dichloromethylene)bisphosphonic acid P'-isopropyl P,P-bis(trimethylsilyl) ester P'-diethylamide ($^{31}$P-NMR (CDCl$_3$): $\delta$−8.92 ppm (P), 14.51 (P'), $^2J_{PP}$=23.7 Hz) is obtained.

The evaporation residue is mixed for 15 rain in 100 ml of anhydrous methanol and the mixture is evaporated under vacuum. The yield is appr. 6.1 g (90% of theor.) of almost colourless crystalline (dichloromethylene) bisphosphonic acid P'-isopropyl ester P'-diethylamide ($^{31}$P-NMR (CDCl$_3$): $\delta$8.37 ppm (P), 15.42 ppm (P'), $^2J_{PP}$=23.0 Hz) at a concentration of >97% and which with sodium hydroxide treatment can be-converted to the corresponding disodium salt ($^{31}$P-NMR (D$_2$O): $\delta$7.93 ppm (P), 21.89 ppm (P'), $^2J_{PP}$=15.7 Hz ).

I.a. the following unsymmetrical (dichloromethylene)bisphosphonic acid ester amides can be prepared in an analogous manner:

From P'-ethyl P,P-dimethyl P'-(benzylmethylamido)(dichloromethylene)bisphosphonate over P'-ethyl P,P-bis(trimethylsilyl) P'-(benzylmethylamido)(dichloromethylene)bisphosphonate P'-ethyl P'-(benzylmethylamido)(dichloromethylene)bisphosphonate which may be further converted to the corresponding disodium salt ($^{31}$P-NMR (D$_2$O): $\delta$7.63 ppm (P), 23.86 ppm (P'), $^2J_{PP}$=15.3 Hz).

EXAMPLE 8

P,P-Bis(diethylaimido)P'-methyl(dichloromethylene)-bisphosphonic acid and its tributylammonium salt 7.66 g (0.02 moles) of P,P-bis(diethylamido) P',P'-dimethyl (dichloromethylene) bisphosphonate (see Example 1) and 3.71 g (0.02 moles) of anhydrous tributylamine are dissolved in 20 ml of anhydrous chloroform. The solution is stirred under reflux for 4 h and the solvent evaporated under vacuum, whereby appr. 11.1 g (98% of theor. ) of P,P-bis (diethylamido) P'-methyl (dichloromethylene) bisphosphonic acid methyl-tributylammonium salt is obtained as a pale stiff yellow oil [$^{31}$P-NMR (CDCl$_3$): $\delta$27.88 ppm (P), 6.17 ppm (P'), $^2J_{PP}$=17.2 Hz, $^3J_{PP}$=10.2 Hz, $^3J_{PH}$=9.0 Hz] at a concentration of 95% and from which the corresponding acid may be liberated with acid treatment.

EXAMPLE 9

(Dichloromethylene)bisphosphonic acid P'-ethyl P-methyl ester P'-benzylmethylamide and its tributylammonium salt 4.40 g (0.01 moles) of (dichloromethylene) bisphosphonic acid P'-ethyl P,P-dimethyl ester P'-benzylmethylamide (see Example 4) is dissolved in 20 ml of anhydrous chloroform and 1.85 g (0.01 moles) of tributylamine is added and stirred under reflux for 4 h (the progress of the reaction is followed with NMR) and evaporated under vacuum. The yield is appr. 5.8 g (100% of theor. ) of oily (dichloromethylene) bisphosphonic acid P'-ethyl P-methyl ester P'benzylmethylamide tributylmethylammonium salt ($^{31}$P-NMR (CDCl$_3$): $\delta$4.94 ppm (P), 18.77 ppm (P'), $^2J_{PP}$=17.9 Hz) at a concentration of >97.% and which can be converted to the corresponding acid with acid treatment.

I.a. the following unsymmetrical (dichloromethylene)bisphosphonic acid ester amides can be prepared in an analogous manner.

From P'-isopropyl P,P-dimethyl P'-(diethylamido)(dichloromethylene)bisphosphonate (see Example 4) the P'-isopropyl P-methyl (diethylamido) (dichloromethylene) bisphosphonate tributylmethylammonium salt (free acid, $^{31}$P-NMR (CDCl$_3$): $\delta$8.53 ppm (P), 15.18 ppm (P'), $^2J_{PP}$=21.1 Hz).

EXAMPLE 10

(Dichloromethylene)bisphosphonic acid (mono)methylamide and its trisodium salt 1.68 g (0.005 moles) of methylenebisphosphonic acid P'-ethyl P,P-dimethyl ester P'-benzylmethylamide (see Example is dissolved in 16 ml of acetic acid and 340 mg of 10% Pd/C is added. The mixture is hydrogenated at room temperature for 2.5 h and the catalyst is removed by filtration. To the filtrate fresh catalyst is added and hydrogenation is continued for 3 h. An additional 340 mg of fresh catalyst and 5 drops of water are added and hydrogenated for 18 h. The mixture is filtered and the filtrate evaporated under vacuum, whereby appr. 0.75 g (60% of theor.) of methylenebisphosphonic acid P'-ethyl P,P-dimethyl ester P'-methylamide ($^{31}$P-NMR (CDCl$_3$): $\delta$24.73 ppm (P), 26.99 (p,) $^2J_{PP}$=5.5 Hz) is obtained at a concentration of >90%. The obtained evaporation residue is chlorinated to form (dichloromethylene)bisphosphonic acid P'-ethyl P,P-dimethyl ester P'-(mono)methylamide ($^{31}$P-NMR (CDCl$_3$): $\delta$10.75 ppm (P), 13.26 (P'), $^2J_{PP}$=23.0 Hz) according to the process of step 2 of Example 1, whereafter the P,P,P'-ester groups are hydrolysed over (dichloromethylene) bisphosphonic acid P,P,P'-tri(trimethylsilyl)ester P'-(mono)methylamide to (dichloromethylene)bisphosphonic acid (mono)methylamide according to the process of Example 1. By treating an acetone solution of the product with three equivalents of a 5N NaOH solution, the corresponding trisodium salt is obtained as a colourless crystalline product.

EXAMPLE 11

(Chloromethylene)bisphosphonic acid P'-ethyl P,P-dimethyl ester P'-benzylmethylamide 2.0 g (0.005 moles) of dichloromethylenebisphosphonic acid P'-ethyl P,P'-dimethyl ester P'-benzylmethylamide (see Example 4) in 20 ml of ethanol is added dropwise at 0° C. to a solution containing 2.4 g of Na$_2$-

SO₃ in 40 ml of water. After the addition the mixture is stirred for 40 min (the progress of the reaction is followed with NMR). When the reaction has ceased, the mixture is extracted with CHCl₃ and the extract washed with water, dried (Na₂SO₄) and filtered. The filtrate is evaporated under vacuum, whereby appr. 1.5 g (80% of theor.) of (chloromethylene)bisphosphonic acid P'-ethyl P,P-dimethyl ester P'-benzylmethylamide is obtained (³¹P-NMR (CDCl₃): δ17.51/17.20 ppm (P), 19.91/19.52 ppm (P'), $^2J_{PP}$=6.7/10.5 Hz diastereomer pair) as an almost colourless oil at a concentration of >90%.

I.a. the following symmetrical and unsymmetrical (chloromethylene)bisphosphonic acid ester amides can be prepared in analogous manner:

From P,P,P'-trimethyl P'-(diethylamido) (dichloromethylene) bisphosphonate (see Example 4) P,P,P',-trimethyl P'-(diethylamido) (chloromethylene) bisphosphonate.

From P,P-dimethyl P', P'-bis (diethylamido) (dichloromethylene)bisphosphonate (see Example 1) P,P-dimethyl P',P'-bis(diethylamido) (chloromethylene) bisphosphonate.

EXAMPLE 12

(Dichloromethylene) bisphosphonic acid P,P'-bis(tertbutyldiphenylsilyl) P-methylester P'-dibutylamide, (Dichloromethylene) bisphosphonic acid P,P'-bis(tertbutyldiphenylsilyl) P-trimethylsilylester P'-dibutylamide and (Dichloromethylene)bisphosphonic acid P,P'-bis(tertbutyldiphenylsilyl) P'-dibutylamide 1.85 (0.005 moles) of (dichloromethylene)bisphosphonic acid P-methyl ester P'-dibutylamide (see Example 6) and 4.12 g (0.015 moles) of tert-butyldiphenylsilyl chloride in 30 ml of anhydrous CH₃CN are stirred for 3 h under reflux and the solvent is evaporated under vacuum. The yield is about 4.0 g (100% of theor.) of (dichloromethylene)bisphosphonic acid P,P'-bis(tert-butyldiphenylsilyl) P-methyl ester P'-dibutyl amide (³¹P-NMR (CDCl₃): δ2.34/2.29 ppm (P), 5.20/4.61 ppm (P'), $^2J_{PP}$=36.8/27.9 Hz, diasteromer pair) at a concentration of >85%.

1.64 g (0. 002 moles) of (dichloromethylene) bisphosphonic acid P,P'-bis (tert-butyldiphenylsilyl) P-methyl ester P'-dibutyl amide is dissolved in 15 ml of anhydrous CH₃CN and 240 mg (0.0029 moles) of chlorotrimethylsilane and 330 mg (0.0022 moles) of NaI are added and the mixture is stirred for 1 h at room temperature and filtered. The filtrate is evaporated under vacuum, whereby appr. 1.7 g ( 95% of theor. ) of (dichloromethylene) bisphosphonic acid P,P'-bis(tert-butyldiphenylsilyl) P-trimethylsilyl ester P'-dibutyl amide is obtained (³¹P-NMR (CDCl₃): δ −7.17/−7.73 ppm (P), 7.46/7.44 ppm $^2J_{PP}$=28.9/31.3 Hz) as a brownish-yellow solid residue at a concentration of >80%.

The evaporation residue is stirred for 15 min in 10 ml of anhydrous CH₃OH and the solution is evaporated under vacuum. The residue is stirred in 20 ml of anhydrous ether and the mixture filtered. The filtrate is evaporated under vacuum, whereby appr. 1.2 g (95% of theor.) of (dichloromethylene) bisphosphonic acid P,P'-bis(tert-butyldiphenylsilyl) P'-dibutyl amide is obtained (³¹P-NMR (CDCl₃): δ0.27/−2.13 ppm (P), 8.45/7.37 ppm (P') $^2J_{PP}$=23.7/32.3 Hz, diastereomer pair) as a pale yellow solid residue at a concentration of >88%.

EXAMPLE 13

(Dibromomethylene)bisphosphonic acid P-ethyl ester P,-P',P'-tris(diethylamide), (Bromomethylene)bisphosphonic acid P-ethyl ester P,P',P'tris(diethylamide) and (Bromochloromethylene)bisphosphonic acid P-ethyl ester P,P'P'-tris(diethylamide)

Into a sodium hypobromite solution which has been prepared by adding 8.4 g of bromine into 4.6 g NaOH in 50 ml of water, 7.4 g (0.02 moles) of methylenebisphosphonic acid P-ethyl ester P,P'P'-tris(diethylamide), to which has been added 50 ml of toluene and 5.0 g of benzyltriethylammonium chloride, is added while stirring (see Example 1) during appr. 10 min, whereafter stirring is continued for 24 h >40° C. The mixture is extracted with CH₂Cl₂ and the extract is washed with water and dried (Na₂SO₄) and filtered. The filtrate is evaporated under vacuum, whereby appr. 5.8 g (55% of theor.) of (dibromomethylene)bisphosphonic acid P-ethyl ester P,P',P'-tris(diethylamide) (³¹P-NMR (CDCl₃): δ16.95 ppm (P), 25.01 ppm (P'), $^2J_{PP}$=16.6 Hz) is obtained at a concentration of >90%.

In the corresponding manner P'-ethyl P,P-dimethyl P'-(benzylmethylamido)methylenebisphosphonate P'-ethyl P,P-dimethyl P'-(benzylmethylamido)(dibromomethylene)bisphosphonate (³¹P-NMR (CDCl₃): δ11.95 ppm (P), 14.54 ppm (P'), $^2_{PP}$=18.1 Hz) can be prepared.

To 4.9 g (0.01 moles;) of (dibromomethylene) bisphosphonic acid P'-ethyl P,P-dimethyl ester P'-benzylmethylamide (see above) in 70 ml of abs. ethanol 2.5 g of SnCl₂×H₂O in 100 ml of water is added while stirring at 0° C., whereafter the stirring is continued for 15 min and the mixture extracted with CHCl₃. The extract is dried (Na₂SO₄) and filtered and the filtrate evaporated under vacuum, whereby appr. 2.9 g (70% of theor. ) of (bromomethylene) bisphosphonic acid P'-ethyl P,P-dimethyl ester P'-benzylmethyl amide is obtained (³¹P-NMR (CDCl₃): δ17.29/17.21 ppm (P), 19.76/19.21 (P'), $^2J_{PP}$=4.5/10.5 Hz, diastereomer pair) at a concentration of >90%.

In the same manner one can from P-ethyl P,P',P'-tris(diethylamido) (dibromomethylene) bisphosphonate prepare P-ethyl P,P', P'-tris (diethylamido) (bromomethylene) bisphosphonate (³¹P-NMR (CDCl₃): δ6.22.79/21.87 ppm (P), 25.37/24.71 ppm (P'), $^2J_{PP}$=2.7/10.1 Hz diastereomer pair).

4.5 g (0.01 moles) of (bromomethylene)bisphosphonic acid P-ethyl ester P,P',P'-tris(diethylamide) is mixed into 50 ml of toluene, to which 3.0 g of benzyltriethylammonium chloride has been added. The mixture is heated to 40°-50° C. and 70 ml of a 10% NaOCl-solution is added. The mixture is stirred intensively for 24 h at 40°-50° C. whereafter the organic phase is separated and the aqueous phase is extracted with 2×50 ml of toluene. The combined toluene phases are washed with 2×10 ml of a saturated NaCl-solution and dried (Na₂SO₄) and filtered. The filtrate is evaporated under vacuum whereby appr. 3.4 g (70% of theor. ) of (bromochloromethylene) bisphosphonic acid P-ethyl ester P,P',P'-tris(diethylamide) is obtained (³¹P-NMR (CDCl₃): δ17.00/17.23 ppm (P), 25.72/25.32 ppm (P'), $^2J_{PP}$=19.2/18.1 Hz diastereomer pair).

We claim:

1. Methylenebisphosphonic acid ester derivatives having the general formula I

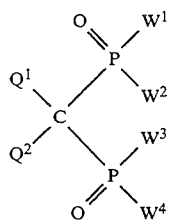

in which formula $W^1$, $W^2$, $W^3$ and $W^4$ are independently the group $OR^1$ or the group $NR^2R^3$ wherein $R^1$, $R^2$ and $R^3$ independently are hydrogen or straight or branched $C_1$-$C_8$ alkyl, benzyl or phenyl, or the groups $R^2$ and $R^3$ form together with the adjacent nitrogen atom a piperidino or morpholino ring, provided that in the formula I at least one of the groups $W^1$, $W^2$, $W^3$ and $W^4$ is hydroxy and at least one of the groups $W^1$, $W^2$, $W^3$ and $W^4$ is the amino group $NR^2R^3$, $Q^1$ is hydrogen or chlorine, and $Q^2$ is chlorine, including the stereoisomers, such as the geometrical isomers and the optically active isomers, of the compounds, as well as the pharmacologically acceptable salts of the compounds.

2. Methylenebisphosphonic acid derivative selected from the group consisting of:
(dichloromethylene)bisphosphonic acid P,P,P'-tris(diethyl amide),
(dichloromethylene)bisphosphonic acid P-monoisopropyl ester P-mono(diethylamide),
(dichloromethylene)bisphosphonic acid P,P-bis(diethylamide),
(dichloromethylene)bisphosphonic acid mono(diethylamide),
(dichloromethylene) bisphosphonic acid mono(phenyl-N-methyl amide),
(dichloromethylene) bisphosphonic acid mono(benzylamide), and
(dichloromethylene) bisphosphonic acid P,P'-bis(diethylamide),
including the stereoisomers, such as the geometrical isomers and the optically active isomers, of the compounds, as well as the pharmacologically acceptable salts of the compounds.

3. Pharmaceutical composition, characterized in that it contains as the active agent a compound of the formula I according to the claim 1.

4. The composition according to the claim 3 wherein the active agent is selected from the group consisting of:
(dichloromethylene)bisphosphonic acid P,P,P'-tris(diethyl amide),
(dichloromethylene)bisphosphonic acid P-monoisopropyl ester P-mono (diethylamide),
(dichloromethylene)bisphosphonic acid P,P-bis(diethylamide),
(dichloromethylene)bisphosphonic acid mono(diethylamide),
(dichloromethylene)bisphosphonic acid mono(phenyl-N-methyl amide),
(dichloromethylene)bisphosphonic acid mono (benzylamide), and
(dichloromethylene)bisphosphonic acid P,P'-bis(diethylamide).

5. A method of treating a physiological disorder relating to the metabolism of calcium or other divalent metals, or to (pyro)phosphate functions, by administering to a patient a pharmacological composition characterized in that it has as an active agent a compound having the formula I according to claim 1.

6. The method according to the claim 5, wherein the active agent is selected from the group consisting of:
(dichloromethylene)bisphosphonic acid P,P,P'-tris(diethyl amide),
(dichloromethylene)bisphosphonic acid P-monoisopropyl ester P-mono(diethylamide),
(dichloromethylene)bisphosphonic acid P,P-bis(diethylamide),
(dichloromethylene)bisphosphonic acid mono(diethylamide)
(dichloromethylene)bisphosphonic acid mono(phenyl-N-methyl amide),
(dichloromethylene) bisphosphonic acid mono (benzylamide), and
(dichloromethylene) bisphosphonic acid P,P'-bis(diethylamide).

* * * * *

UNITED STATES PATENT AND TRADEMARK OFFICE
CERTIFICATE OF CORRECTION

PATENT NO. : 5,442,101
DATED : August 15, 1995
INVENTOR(S) : Hanhijarvi, et. al.

It is certified that error appears in the above-indentified patent and that said Letters Patent is hereby corrected as shown below:

Col. 10, line 23 - Delete "$2_{pp}$" and substitute -- $^2J_{pp}$ --

Col. 12, line 29 - before "ethyl ester" insert -- P'- --

Col. 13, line 25 - before "21.3" insert -- $^2J_{pp}=$ --

Col. 13, line 30 - delete "($3^1$P-NMR" and substitute -- ($^{31}$P-NMR --

Col. 14, line 17 - delete "methyl" and substitute -- P-methyl --

Col. 15, line 31 - delete "rain" and substitute -- min --

Col. 16, line 36 - after "Example" insert -- 1) --

Col. 18, line 32 - delete "$2_{pp}$" and substitute -- $^2J_{pp}$ --

Col. 18, line 51 - delete "$\S$ 6.22.79" and substitute -- $\S$ 22.79 --

Signed and Sealed this

Second Day of July, 1996

Attest:

BRUCE LEHMAN

Attesting Officer    Commissioner of Patents and Trademarks